United States Patent [19]

Gillis

[11] 4,401,756

[45] Aug. 30, 1983

[54] PROCESS FOR PREPARING HUMAN INTERLEUKIN 2

[75] Inventor: Steven Gillis, Woodinville, Wash.

[73] Assignee: Immunex Corporation, Seattle, Wash.

[21] Appl. No.: 249,905

[22] Filed: Apr. 14, 1981

[51] Int. Cl.³ .................. C12P 21/00; C12N 5/00; C12N 5/02; C12R 1/91; C12P 1/00; C12P 21/02 A61K 37/00

[52] U.S. Cl. .................................. 435/68; 435/240; 435/241; 435/948 435/41; 435/70; 424/177

[58] Field of Search ................ 435/68, 240, 948, 241, 435/41, 70; 424/177

[56] References Cited

PUBLICATIONS

Morgan et al., "Selective in vitro Growth of T Lymphocytes from Normal Human Bone Marrows", 193 *Science* 1007 (1976).

Ruscetti et al., "Functional and Morphological Characterization of Human T Cells Continuously Grown in vitro", 119 *The Journal of Immunology*, 131 (1977).

Gillis et al., "Long Term Culture of Tumor-Specific Cytotoxic T Cells", 268 *Nature* 154 (1977).

Gillis et al., "T-Cell Growth Factor: Parameters of Production and a Quantitative Microassay for Activity", 120 *The Journal of Immunology* 2027 (1978).

Farrar et al., "Biological Relationship of Thymocyte Mitogenic Factor and Factors Enhancing Humoral and Cell-Mediated Immune Responses", 121 *The Journal of Immunology* 1353 (1978).

Watson et al., "Biochemical and Biological Characterization of Lymphocyte Regulatory Molecules-I, Purification of a Class of Murine Lymphokines", 150 *The Journal of Experimental Medicines* 849, (1979).

Gillis et al., "Biochemical Characterization of Lymphocyte Regulatory Molecules-II, Purification of a Class of Rat and Human Lymphokines", 124 *The Journal of Immunology*, 1954 (1980).

Gillis and Watson J. Exp. Med. 152, 1709 (1980).

Farrar and Fuller-Bonar Fed. Proc. 39, 802 (1980).

Gillis, Smith, Watson J. Immunology 124, 1954 (1980).

Gillis, Scheid, Watson Chem. Abstr. 94, 28660 (1981).

Farrar, Simon, Koopman, Fuller-Bonar J. Immunology 121, 1353 (1978).

Watson, Gillis, Marbrook, Mochizuki, Smith J. Exp. Med. 150, 849 (1979).

Watson, Mochizuki, Gillis, Chem. Abstr. 96, 33000 (1981).

*Primary Examiner*—Alvin E. Tanenholtz
*Assistant Examiner*—James Martinell
*Attorney, Agent, or Firm*—Christensen, O'Connor, Johnson & Kindness

[57] ABSTRACT

A process for preparing IL-2 from human malignant cells includes culturing human leukemia or lymphoma cells in vitro in a serum containing medium supplemented with various additives. The culture is stimulated by an optimum concentration of a T cell mitogen to produce a supernate which contains IL-2. After a period of time, the supernate is collected and processed to purify the IL-2. Phorbol myristate acetate may be added to the culture medium to boost production of IL-2.

14 Claims, No Drawings

PROCESS FOR PREPARING HUMAN INTERLEUKIN 2

DESCRIPTION

1. Technical Field

The present invention relates to a process for preparing human interleukin 2 (hereinafter "IL-2"), formerly known in the literature as "T cell growth factor" or "TCGF", and more particularly to a process for producing IL-2 from human malignant cells.

2. Background Art

IL-2 is a soluble protein which is capable of modulating lymphocyte reactivity and promoting the long-term in vitro culture of antigen-specific effector T-lymphocytes (mitogenesis) and, in the past, has been produced by stimulating mouse, rat or human lymphocyte cells with a mitogen. For instance, Morgan et al. in "Selective in vitro Growth of T Lymphocytes from Normal Human Bone Marows", 193 *Science* 1007 (1976) and Ruscetti et al. in "Functional and Morphological Characterization of Human T Cells Continuously Grown in vitro", 119 *The Journal of Immunology* 131 (1977), both discussed a process for culturing pooled normal human lymphocytes in Rosewell Park Memorial Institute (hereafter "RPMI") medium containing autologous serum and the mitogen phytohemagglutinin (hereafter "PHA").

Gillis and Smith, in "Long Term Culture of Tumor-Specific Cytotoxic T Cells", 268 *Nature* 154 (1977) reported preparing murine IL-2 by stimulating normal DBA/2 mouse spleen cells with the mitogen concanavalin A (hereafter "Con A") in an RPMI 1640 culture medium containing fetal calf serum (hereafter "FCS").

Farrar et al. in "Biological Relationship of Thymocyte Mitogenic Factor and Factors Enhancing Humoral and Cell-Mediated Immune Responses", 121 *The Journal of Immunology* 1353 (1978), also disclosed preparing IL-2 from murine spleen cells incubated with Con A in a tissue culture medium containing normal mouse serum (hereafter "NMS").

Gillis et al. reported generating IL-2 from murine and rat spleen cells cultured in a RPMI 1640 tissue culture medium supplemented with heat-inactivated FCS, penicillin-G, and gentamycin. The murine and rat spleen cells were stimulated by various mitogens including Con A, PHA, and pokeweed mitogen (hereafter "PKM"), "T-Cell Growth Factor: Parameters of Production and a Quantative Microassay for Activity", 120 *The Journal of Immunology* 2027 (1978).

IL-2 has also been prepared from human peripheral blood mononuclear cells by culturing the cells in RPMI 1640 medium supplemented with autologous human serum, penicillin, gentamycin, fresh L-glutamine, and PHA. Gillis et al., "Biochemical Characterization of Lymphocyte Regulatory Molecules-II. Purification of a Class of Rat and Human Lymphokines", 124 *The Journal of Immunology* 1954 (1980).

Gillis et al. in "Biochemical and Biological Characterization of Lymphocyte Regulatory Molecules-III. The Isolation and Phenotypic Characterization of Interleukin-2 Producing T Cell Lymphomas", 125 *The Journal of Immunology*, 2570, (1980), identified the preparation of IL-2 from T cell leukemia and lymphoma cell lines, specifically a radiation-induced splenic lymphoma from the B10.BR mouse (LBRM-33) cultured in RPMI 1640 supplemented with heat inactivated FCS, $2.5 \times 10^{-5}$ M 2-mercaptoethanol, N-2-hydroxy-piperazine-XI[1]-2-ethene-sulfonic acid (hereafter "Hepes") buffer, penicillin, streptomycin and fresh L-glutamine. The cultures were stimulated with various mitogens including Con. A, and PHA.

IL-2 purified from these mouse, rat and human normal T-lymphocytes, has been found to retain different types of biological activity, including: (1) marked enhancement of thymocyte mitogenesis, Watson et al., "Biochemical and Biological Characterization of Lymphocyte Regulatory Molecules-I. Purification of a Class of Murine Lymphokines", 150 *Journal of Experimental Medicine* 849, (1979) and Gillis et al. supra, 124 *Journal of Immunology* 1954 (1980); (2) promotion of long term in vitro proliferation of antigen specific helper or killer T cell lines, Gillis et al., supra, 268 Nature 154 (1977) and Watson, "Continuous Proliferation of Murine Antigen Specific Helper T Lymphocytes in Culture", 150 *Journal of Experimental Medicine* 1510 (1979); and (3) induction of cytotoxic T lymphocyte (hereafter "CTL") reactivity and plaque-forming cell responses in cultures of nude mouse spleen cells. Watson et al., supra, 150 *Journal of Experimental Medicine* 849 (1979) and Gillis et al., supra, 124 *The Journal of Immunology* 1954 (1980). Accordingly, these identified biological activities of IL-2 indicate that IL-2 is useful in elevating immune responses and restoring immune deficient T cell populations (nude mouse spleen cells) to normal levels of cell and humoral immunity. Furthermore, these results suggest that IL-2 production and response are important parameters of immunological functions which may be useful in clinical diagnosis of aberrant immunity. Moreover, the fact that human IL-2 makes possible the in vitro proliferation of antigen specific human, mouse and rat killer T cells emphasizes the importance of human IL-2 as a research reagent.

The above cited articles by Morgan et al., 193 Science 1007 (1976); Ruscetti et al., 119 *The Journal of Immunology* 131 (1977); and Gillis et al., 124 *The Journal of Immunology* 1954 (1980), discuss production of human IL-2 from lectin stimulated human splenic and peripheral blood lymphocyte conditioned media. However, these production sources and techniques result in weak concentrations of IL-2, with purification of IL-2 requiring fractionation of large volumes of conditioned media containing IL-2 in order to obtain only very small quantities of human IL-2 activity. As a consequence, sufficient quantities of concentrated human IL-2 have not been available for in vivo experiments, nor to study effectively the final molecular characterization of this lymphocyte regulatory molecule. Accordingly, a principal object of the present invention is to identify cell lines which are potent producers of human IL-2 and also to ascertain the particular conditions and specific mitogens which foster optimum production of human IL-2 from such identified cell lines.

DISCLOSURE OF THE INVENTION

The present invention relates to a process for preparing IL-2 from human malignant cells as set forth by Gillis et al. in "Biochemical and Biological Characterization of Lymphocyte Regulatory Molecules-V. Identification of an Interleukin 2-Producing Human Leukemia T Cell Line", 152 *Journal of Experimental Medicine* 1709 (1980). The process includes culturing malignant neoplastic cells, such as human leukemia and lymphoma cells in vitro, in a serum containing medium supplemented with various additives. The culture is stimulated by a T cell mitogen thereby producing a supernate which contains IL-2. After a period of time, the supernate is collected and processed to purify the IL-2.

The above process has been used in conjunction with a particular leukemic human T-cell line known as Jurkat-FHCRC. Use of the Jurkat-FHCRC leukemic human T cells in a culture medium composed of Click's medium together with certain additives and a plant mitogen, such as PHA or Con. A has been found to produce between 100 to 300 times the amount of human IL-2 per milliliter than previously generated by lectin stimulation of identical numbers of human peripheral blood lymphocytes. Applicant has established that the initial cell concentration of the particular T leukemic or T lymphoma cell used affects the volume of IL-2 production. The concentration of the particular plant mitogen used also influences IL-2 production.

The primary component of the culture medium may consist of commercially available media, such as RPMI medium and Click's medium. Additives which may be added individually or in combination added to the culture medium include penicillin, streptomycin, fresh glutamine, Hepes buffer, $NaHCO_3$, and FCS.

An unsaturated fatty acid derivative of crotin oil (phorbol esters) may be added to the culture medium to boost production of IL-2. For instance, phorbol myristate acetate (herafter "PMA") added to a culture medium containing Jurkat-FHCRC cells stimulated by an optimum 1% by volume concentration of PHA has been found to increase IL-2 production by approximately 100% over IL-2 produced under similar conditions but without the addition of PMA. Also, adding PMA to a 1/10 optimum concentration of PHA mitogen, i.e., 0.1% by volume, has been found to boost IL-2 production back up to the level produced when an optimum concentration of PHA alone is used.

Best Mode of the Invention

Outline of Process

In accordance with the present invention, human malignant neoplastic cells in the form of leukemia and lymphoma cells are cultured in vitro in a protein containing medium supplemented with various additives. T cell mitogen is added to the culture medium to stimulate production of a supernate which contains IL-2. After a period of time, the supernant is collected and processed to purify the IL-2 into a more concentrated form. Also, in accordance with the present invention, to produce IL-2 from human tumor cell lines, a phorbol ester, for instance PMA, may be used as a stimulant either alone or in combination with a T cell mitogen to enhance the production of IL-2. The process of the present invention has been described by Gillis et al. in "Biochemical and Biological Characterization of Lymphocyte Regulatory Molecules V. Identification of an Interleukin 2-Producing Human Leukemia T Cell Line", 152 Journal of Experimental Medicine 1701 (1980).

Applicant has used the above process in conjunction with various leukemic T and B cell lines and also in conjunction with various T lymphoma cell lines wherein the cell lines were produced by either spontaneous occurrence, viral infection or by a chemical carcinogen. Cell lines designated SKI were obtained from the Memorial Sloan-Kettering Cancer Center. Cell lines, designated FHCRC, were obtained from the Fred Hutchinson Cancer Research Center, Seattle, Washington. Of the various human T and B leukemia cell lines tested, as set forth in Table I below, one particular cell line, labeled as Jurkat-FHCRC, was found to produce several times the amount of human IL-2 per milliliter than had been previously generated by equivalent numbers of mitogen-stimulated human peripheral blood lymphocytes (hereinafter PBL) or spleen cells using the processes discussed above.

TABLE I

Screening of Cultured Human T and B Cell Leukemias for IL-2 Production

| | IL-2 Activity Present in 48-h supernate after activation with | | | |
|---|---|---|---|---|
| | Medium* | Con-A | PHA | PKM |
| T cell leukemias | | | | |
| CEM-SKI | 0.0 | 0.0 | 0.0 | 0.0 |
| CEM-FHCRC | 0.0 | 0.0 | 0.0 | 0.0 |
| 8402-FHCRC | 0.0 | 0.0 | 0.0 | 0.0 |
| HSB2-SKI | 0.0 | 0.0 | 0.0 | 0.0 |
| HSB2-FHCRC | 0.0 | 0.0 | 0.0 | 0.0 |
| Molt-4 SKI | 0.0 | 0.0 | 0.0 | 0.0 |
| Molt-4 FHCRC | 0.0 | 0.0 | 0.0 | 0.0 |
| Ke37-FHCRC | 0.0 | 0.0 | 0.0 | 0.0 |
| T-45-SKI | 0.0 | 0.0 | 0.0 | 0.0 |
| R-2-SKI | 0.0 | 0.0 | 0.0 | 0.0 |
| Peer-SKI | 0.0 | 0.0 | 0.0 | 0.0 |
| HPB-ALL-SKI | 0.0 | 0.0 | 0.0 | 0.0 |
| Jurkat-FHCRC | 0.0 | 93.7 | 225.0 | 52.1 |
| B cell leukemias | | | | |
| Daudi-SKI | 0.0 | 0.0 | 0.0 | 0.0 |
| Nalm-1 SKI | 0.0 | 0.0 | 0.0 | 0.0 |
| 8866-FHCRC | 0.0 | 0.0 | 0.0 | 0.0 |
| AR-77-SKI | 0.0 | 0.0 | 0.0 | 0.0 |

*RPMI-1640, 10% FCS
10 μg/ml.
1.0% by volume
1/100 dilution

Applicant has found that the initial cell density of a particular malignant cell line used in the culture process affects the quantity of IL-2 produced by mitogen stimulation per number of initial cells. For instance, as set forth in Table II below, in the Jurkat-FHCRC cell line, when beginning with a cell concentration of $5 \times 10^4$ cells per milliliter, 10 units of IL-2 per milliliter are produced after twenty-four hours when the cells are stimulated with a one percent by volume concentration of PHA. If the initial cell concentration is increased to approximately $1.0 \times 10^6$ cells per milliliter, a maximum of approximately 225 units of IL-2 per milliliter is produced. However, further increasing the concentration of Jurkat-FHCRC cells to, for instance, $1.0 \times 10^7$ cells per milliliter, causes the production of IL-2 to drop back down to approximately 103 units per milliliter. Thus, if Jurkat FHCRC cells are used, the initial density of the cells preferably should be in the range of about $5 \times 10^5$ cells/ml to $1 \times 10^7$ cells/ml, with an ideal concentration of approximately $1 \times 10^6$ cells/ml.

TABLE II

Jurkat-FHCRC-derived IL-2 Production: Optimal Concentration

| Jurkat-FHCRC cell concentration | IL-2 activity present in 24-h supernate after 1% PHA stimulation U/ml |
|---|---|
| $10^7$/ml | |
| $5 \times 10^6$/ml | 151 |
| $2 \times 10^6$/ml | 193 |
| $10^6$/ml | 225 |
| $5 \times 10^5$/ml | 178 |
| $2 \times 10^5$/ml | 53 |
| $10^5$/ml | 26 |
| $5 \times 10^4$/ml | 10 |

The human malignant cell lines, and particularly the Jurkat-FHCRC leukemia cell, may be grown in cell culturing media which have been previously found to foster growth of T-cells. These culture media include RPMI-1640, Click's medium and Dulbecco Modified Eagle Medium (hereinafter "DMEM"). These culture media may be supplemented with various individual additives or combinations of additives, including FCS or normal human serum which has been heat-inactivated by, for example, applying heat at 56° C. for 30 minutes. The volume of FCS or normal human serum added may be from 2 to 10 percent of the total culture volume. Another additive is penicillin in a concentration range of approximately 20 to 250 units per milliliter, and preferably approximately 50 units per milliliter. Streptomycin may also be utilized as an additive in a preferred concentration range of from 20 to 250 micrograms per milliliter, and ideally approximately 50 micrograms per milliliter. Further additives include: (i) fresh L-glutamine in a preferred concentration range of approximately 100 to 1000 micrograms per milliliter, with an ideal concentration of approximately 300 micrograms per milliliter; (ii) Hepes buffer in a preferred concentration of from 10 to 60 mM, and ideally 25 mM; and (iii) $NaHCO_3$ in a preferred concentration range of from 8 to 20 mM, and ideally approximately 16 mM.

In the IL-2 production process of the present invention, several different stimulating mitogens may be utilized. These mitogens include plant glycoproteins such as Con A, PHA and PKM. Applicant has found that the specific concentration of the particular mitogen used affects the amount of IL-2 produced. For instance, as set forth in Table III below, if Jurkat-FHCRC cells at a concentration of $1 \times 10^6$ cells per milliliter are stimulated with a concentration of 1.0 microgram per milliliter of Con A, in approximately twenty-four hours about 8 units per milliliter of IL-2 are produced. When 20 micrograms per milliliter of Con A are employed, approximately 207 units of IL-2 per milliliter are obtained. If the concentration of Con A is further increased to 100 micrograms per milliliter, IL-2 production decreases to 124 units per milliliter which is still several hundred times the quantity of IL-2 produced by Con A stimulation of an equivalent number of human peripheral blood lymphocytes. Accordingly, when Con A is used as a mitogenic stimulant for Jurkat-FHCRC cells at a concentration of $1 \times 10^6$ cells per milliliter, an optimum concentration of Con A is from approximately 20 to 100 micrograms per milliliter. It is to be understood that if different concentrations of Jurkat-FHCRC cells are employed, or if another cell line is used, the optimum concentration of Con A may have to be empirically determined to obtain maximum IL-2 production.

TABLE III

| Jurkat-FHCRC-derived IL-2 Production: Mitogen Dose Responses | | |
|---|---|---|
| Mitogen | Concentration | IL-2 activity* U/ml |
| PHA | 10% | 101 |
| PHA | 5% | 135 |
| PHA | 2% | 171 |
| PHA | 1% | 252 |
| PHA | 0.5% | 234 |
| PHA | 0.2% | 117 |
| PHA | 0.1% | 39 |
| Con A | 100 μg/ml | 124 |
| Con A | 50 μg/ml | 171 |
| Con A | 20 μg/ml | 207 |

TABLE III-continued

| Jurkat-FHCRC-derived IL-2 Production: Mitogen Dose Responses | | |
|---|---|---|
| Mitogen | Concentration | IL-2 activity* U/ml |
| Con A | 10 μg/ml | 121 |
| Con A | 5 μg/ml | 14 |
| Con A | 2 μg/ml | 11 |
| Con A | 1 μg/ml | 8 |

*24-h supernate assayed on murine CTLL cells.

As indicated in Table III above, the particular concentration of PHA mitogen added to a Jurkat-FHCRC cell culture also affects the quantity of IL-2 produced per initial cell concentration of the Jurkat-FHCRC cells. For instance, stimulation of Jurkat-FHCRC cells at a concentration of $10^6$ cells per milliliter with a 0.1% concentration of PHA has been found to result in IL-2 activity in the amount of 39 units per milliliter. However, if the PHA concentration is increased to approximately 1.0%, a maximum quantity of 252 units per milliliter of IL-2 is produced. Increasing the PHA concentration to above this level has been found to affect negatively IL-2 production. For example, when the PHA concentration is increased to 10% by volume, the IL-2 activity drops down to approximately 101 units per milliliter. Accordingly, for optimum stimulation of Jurkat-FHCRC cells at a concentration of approximately $1 \times 10^6$ cells per milliliter, a PHA mitogen concentration in the range of 0.5% to 2% by volume should be used, with the ideal concentration being approximately 1% by volume.

The above-described process for producing IL-2 from human malignant cell lines, such as leukemic Jurkat-FHCRC cells, may be carried out in various environmental conditions. Preferably, however, the Jurkat-FHCRC culture should be maintained at a temperature range of approximately 35° to 38° C. and in a humidified atmosphere of from approximately 5 to 10% carbon dioxide in air. Also, ideally the pH of the culture medium should be kept in slightly alkaline condition, in the range of approximately pH 7.0 to 7.4.

The malignant cell lines may be seeded in different types of containers including flat-bottom microplate wells and in various sizes such as in 100-microliter aliquots. Tissue culture flasks, such as flasks No. 3013 or 3025 from Falcon Labware, Div. Becton, Dickinson and Co. also may be used. Alternatively, a roller bottle, such as bottle No. 3027 also from Falcon Labware, may be used as a container for the culture.

The quantity of IL-2 produced by stimulating malignant human cells with a plant mitogen varies with time. For instance, when $10^6$ Jurkat-FHCRC cells are cultured in Click's medium and stimulated with a 1% by volume concentration of PHA, IL-2 activity first appears in the culture at about five to seven hours after PHA stimulation. Peak levels of IL-2 are reached at approximately sixteen to twenty-four hours after stimulation by PHA. Moreover, during the subsequent twenty-four hour period, the quantity of IL-2 present diminishes only slightly. Thus, the optimum culture duration for producing IL-2 with Jurkat-FHCRC cells in a RPMI-1640 medium activated with 1% by volume PHA is approximately from sixteen to forty-eight hours.

Production of IL-2 from human malignant cell lines may be boosted by adding phorbol esters, such as PMA, to one of the plant mitogens listed above. For instance, it has been found that when Jurkat-FHCRC cells in an optimum concentration of $10^6$ cells per milliliter are cultured in RPMI-1640 supplemented with 10% by volume FCS and stimulated with 1% by volume PHA, if PMA is added at a concentration of 10 nanograms per milliliter, after twenty-four hours the IL-2 activity is increased by approximately 250 units per milliliter over the amount of IL-2 produced under similar conditions but without the addition of PMA (see Table IV below). Moreover, if PMA at a concentration of 10 nanograms per milliliter is added to a sub-optimum concentration of 0.1% PHA, IL-2 production is restored from approximately 39 units per milliliter back up to 178 units per milliliter which is approximately equal to the activity level of IL-2 produced when an optimum concentration of 1% PHA is utilized alone. Thus, adding PMA to the malignant cell culture significantly reduces the concentration of mitogen needed to produce a given level of IL-2. This has the advantage of requiring less effort to remove the mitogen contamination during purification of the IL-2. Applicant has also found that the use of PMA alone in a concentration of 10 nanograms per milliliter, without any mitogen stimulant, causes production of IL-2 from Jurkat-FHCRC cells within twenty-four hours at an activity level of approximately 65 units per milliliter. Accordingly, it appears that although IL-2 production may be enhanced by the addition of PMA, for efficient IL-2 production, PMA cannot serve as a complete substitute for an appropriate plant mitogen.

TABLE IV

Effect of PMA on Jurkat-FHCRC Cell Line IL-2 Production

| Jurkat-FHCRC cells stimulated with* | | | IL-2 activity present in |
|---|---|---|---|
| 1% PHA | 0.1% PHA | PMA (10 ng/ml) | 24-h conditioned medium |
| − | − | − | 0.0 ± 0.0 |
| − | − | + | 65.0 ± 17.0 |
| − | + | − | 39.0 ± 3.6 |
| + | − | − | 210.0 ± 16 |
| − | + | + | 178 ± 42 |
| + | − | + | 462.0 ± 76 |

*$10^6$ cells/ml in RPMI-1640 10% FCS.
Mean ± 1 SD IL-2 (U/ml) activity present in supernates harvested from three separate experiments.
−, not present in culture; +, denotes present in culture.

Microassay of IL-2

The activity levels of IL-2 produced by the mitogen and/or phorbol ester stimulation of various malignant human cell lines, may be ascertained by using the microassay procedure discussed by Gillis et al. in "T-Cell Growth Factor: Parameters of Production and a Quantative Microassay for Activity", 120 *The Journal of Immunology* 2027 (1978). The assay monitors the IL-2 dependent cellular proliferation of a mouse cytotoxic T cell line (hereafter "CTLL"). Once potential combinations of cell lines and mitogens are identified, such as Jurkat-FHCRC stimulation by PHA, the microassay technique is then employed to determine optimum culture conditions for IL-2 production, such as the optimum initial cell concentration of Jurkat-FHCRC and optimum mitogen doses, as discussed above.

Briefly, the microassay procedure includes seeding approximately 3000 CTLL cells in 200-microliter volumes in a $\log_2$ dilution series of potential IL-2-containing samples. The mixture is cultured for twenty-four hours at 37° C. in a humidified atmosphere of 5% carbon dioxide in air. Thereafter, the cultures are pulsed for approximately four hours with 0.5 microcuries of tritiated thymidine ([$^3$H]Tdr; 20 mCi/mM specific activity) after which time the cultures are harvested onto glass fiber filter strips, for instance with the aid of a multiple automated sample harvester. [$^3$H]Tdr incorporation is then measured by liquid scintillation counting. By this procedure, only the CTLL cells cultured in the presence of IL-2 were found to incorporate [$^3$H]Tdr in a dose-dependent manner. CTLL cells cultured in the absence of IL-2 incorporated only scintillant control levels of [$^3$H]Tdr and were more than 95% trypan-blue positive after twenty-four hours of IL-2 deprivation. Units of IL-2 activity were determined by probit analysis of [$^3$H]Tdr incorporation data. A 1 unit/ml standard has been defined as the amount of IL-2 activity present in 48 hour tissue culture medium conditioned by Con A (5 microgram/ml) stimulation of an initial concentration of $10^6$ cells per milliliter of normal rat spleen cells. An assay of 1 unit/ml standard routinely stimulated approximately 10,000 cpm of CTLL [$^3$H]Tdr incorporation at a dilution of 1:2. The results of the microassay of the culture fluids from various human cell lines stimulated by different mitogens is set forth above in Table I.

Biochemical Characterization of Human IL-2

IL-2 may be concentrated and/or purified from culture supernates by various procedures including salt precipitation, vacuum dialysis, gel filtration chromotography, ion exchange chromatography, preparative flat-bed iso-electric focusing (hereafter "IEF") and gel electrophoresis. Methods for concentration/purification of IL-2 activity are described in Watson et al., supra, 150 *Journal of Experimental Medicine* 849 (1979), Gillis et al., supra, 124 *The Journal of Immunology* 1954 (1980), Mochizuki et al., "Biochemical Separation of Interleukin 2", 39 *Journal of Immunological Methods* 185 (1980) and Watson et al., "Purification of T-cell Replacing Factors and T-cell Growth Factors" in *Pharmacology of the Reticuloendothelial System*, editor D. Webb, New York: Marcel Dekker Press, 1981.

To determine the biochemical characteristics of human IL-2 from the Jurkat-FHCRC cell line, culture supernates were subjected to standard biochemical separation protocols (see Example 2 below, and the references set forth immediately above). Using these procedures human IL-2 was found to be precipitated from supernates by addition of solid ammonium sulfate to a final concentration of 85% (weight/volume). Human IL-2 activity was eluted from gel filtration chromatography columns (using Sephadex G-100 separation resin obtained from either Pharamacia Fine Chemicals, Inc., Piscataway, N.J.; or ACA54 separation resin obtained from LKB, Inc., Bromma, Sweden); with molecules in the size range of 15,000–25,000 daltons. Further purification of the gel chromotography eluted IL-2, revealed that human IL-2 activity did not bind to di-ethyl amino ethyl (hereafter "DEAE") cellulose equilibrated in a buffer of 0.05 M NaCl. Preparative IEF of IL-2 purified by successive gel filtration and ion exchange chromatography procedures revealed that the human IL-2 activity had an isoelectric point of pH 6.4–6.6 (Gillis et al. supra, 124 *The Journal of Immunology* 1954 (1980). Finally, gel electrophoresis of IEF-purified IL-2, revealed that human IL-2 biological activity was contained in a protein fraction corresponding to 12,000–15,000 daltons. In summary, the biochemical characterization of IL-2 produced by Jurkat-FHCRC cells was found to be almost identical to IL-2 produced by mitogen stimulated human peripheral blood lymphocytes. This was determined using the procedures set forth above and discussed in greater detail in Example 2.

Human IL-2 was also determined to be a proteinaceous substance. This was ascertained by both physical and enzymatic testing. It was observed that after reduction with 2-mercaptoethanol and di-thiothreitol (1 mM) IL-2 activity remained stable. Both human peripheral blood lymphocyte and Jurkat-FHCRC generated IL-2 activity was found to be resistant to treatment with DNAse and RNAse. However, human IL-2 activity was abolished by treatment with the following enzymes: trypsin, chymotrypsin, subtilisin and leucine amino peptidase. Such protease sensitivity is consistent with the conclusion that IL-2 is a proteinaceous substance.

Further tests with conventional human peripheral blood lymphocytes and Jurket-FHCRC cell derived IL-2 determined that the purified lymphokine does not cause fresh peripheral blood lymphocytes to proliferate; but does induce proliferation in T-lymphocyte populations previously stimulated with lectins or specific antigens. Moreover, human IL-2 was found to maintain the proliferation of not only human antigen-specific effector T-cells, but also murine antigen-specific effector T-cells. As such, the Jurkat-FHCRC produced IL-2 is a valuable reagent for use in the growing of clonal human and murine T-cells with various antigens and effector specifications.

EXAMPLES 1A, 1B and 1C

Cell line samples of human leukemic T-cells, Jurkat-FHCRC, in a concentration of $2 \times 10^6$ cells per milliliter were cultured in replicate flat-bottom microplate wells (3596; Costar, Data Packaging, Cambridge, Massachusetts), in Click's medium. The medium was supplemented with 10% by volume, heat-inactivated (56 degrees centigrade for 30 minutes) FCS, 25 mM Hepes buffer, 16 mM NaHCO$_3$, 50 units per milliliter penicillin, 50 micrograms per milliliter streptomycin, and 300 micrograms per milliliter of fresh L-glutamine. The size of each culture, including the cell line sample, medium and supplements totaled 100 microliters. The microwell cultures were then stimulated by adding 100 microliters of: (Example 1A) Con A in a concentration of 40 micrograms per milliliter (Miles Biochemicals, Inc., Elkhart, Indiana); (Example 1B) PHA at a concentration of 2% by volume (PHA-M, Grand Island Biological Co., Grand Island, NY); and, (Example 1C) PKM at 1/50 dilution (Grand Island Biological Co.). The cultures were all maintained at approximately 37 degrees centigrade in a humidified atmosphere of 5% carbon dioxide in air.

After 48 hours, the supernate samples from the cultures were pooled and assayed for IL-2 activity using the microassay procedure as detailed above. The assay determined that IL-2 activity present in the 48 hour supernate included 93.7 units per milliliter for the culture activated with Con A, 225 units per milliliter for the culture activated by PHA, and 52.1 units per milliliter from the culture activated with PKM.

EXAMPLE 2

Jurkat-FHCRC cells at a cell density of $1 \times 10^6$ cells per milliliter (100 milliliter volumes) were suspended in several tissue culture flasks (No. 3024 from Falcon Labware, Div. Becton, Dickinson & Co., Oxnard, CA) in a humidified atmosphere of 5% carbon dioxide in air. RPMI-1640 was used as a medium. This medium was supplemented with 2% FCS (volume by volume), 50 units per milliliter of penicillin, 50 micrograms per milliliter of streptomycin, 300 micrograms per millimeter of fresh glutamine, 25 milliliters per mole of Hepes buffer, and 15 milliliters per mole of NaHCO$_3$. PHA (PHA-M Gibco) in a concentration of 1% by volume and PMA (10 nanograms milliliters) were used as stimulants. After twenty-four hours of culture, the supernate was centrifuged at 3000 xg for 10 minutes. IL-2 in a concentration of 315 units per milliliter was produced.

The IL-2 produced was purified by the following procedures:

Ammonium sulfate precipitation/concentration 500 milliliters of supernate were filtered through a 0.45 micron filter to remove debris. Thereafter, solid ammonium sulfate was added slowly at 4° C. to produce an 85% saturated solution. The supernate and ammonium sulfate solution was stirred slowly for 12 hours at 4° C. Thereafter, the mixture was centrifuged at 10,000 xg for 20 minutes. The resulting supernate was discarded and the precipitate was resuspended in 50 milliliters at 0.9% NaCl, buffered with 25 mM Hepes at pH 7.4 (hereafter 0.9 NaCl-Hepes). This solution (containing approximately 80–90% of all IL-2 activity in the original Jurkat-FHCRC conditioned medium) was dialysed against 100 volumes of 0.9% NaCl-Hepes for twenty-four hours at 4° C.

Gel Filtration Chromotography

The dialysed concentrate obtained from the ammonium sulfate precipitation was applied to a column $(2 \times 90$ cm) of Sephadex G-100 (Pharmacia Fine Chemicals, Piscataway, N.J.) which was previously equilibrated with 0.9% NaCl-Hepes. IL-2 activity was eluted with an additional amount of 0.9% NaCl-Hepes and collected in 100 separate 6 milliliter fractions. The protein content of the column fractions was monitored using an LKB Uvicord II (LRB, Bromma, Sweden) calibrated for absorbance at 280 nanometers. The column was calibrated using the following molecular weight standards: bovine serum albumin (68,000 daltons); ovalbumin (43,000 daltons); soybean trypsin inhibitor (22,000 daltons) and cytochrome C (12,000 daltons). IL-2 microassay tests of each column fraction revealed that IL-2 activity was contained in fractions corresponding to a molecular weight of from 12,000 to 25,000 daltons. These fractions were pooled and dialysed against 100 volumes of 50 mM NaCl-Hepes.

Ion Exchange Chromatography

Pooled, dialysed Sephadex G-100 fractionated IL-2 was applied to a column $(1.5 \times 40$ cm) of DEAE cellulose previously equilibrated in 50 mM NaCl-Hepes. From 20 to 50 milliliters of the IL-2 solution was applied to the column. After washing the column with 70 milliliters of buffer (the filtrate was collected in 20 separate 3.5 milliliter fractions), the protein bound to DEAE cellulose was eluted with a salt gradient (140 milliliters) of 50 to 500 mM NaCl-Hepes and collected in 40 additional 3.5 milliliter fractions. The ionic strength of each fraction was determined using a conductivity meter (type CDM, The London Company, Cleveland, OH). An IL-2 microassay of each column fraction revealed that IL-2 activity did not bind to DEAE cellulose and could be recovered in run-thru fractions containing 50 mM NaCl-Hepes. Active fractions were pooled and dialysed against 100 volumes of 1% by weight glycine prior to IEF.

Preparation IEF

Flat-bed IEF of pooled Sephadex G-100 and DEAE cellulose chromatography fractionated IL-2 was performed in horizontal layers of Sephadex using an LKB Multiphor apparatus (LKB, Bromma, Sweden). The IL-2 preparation was made in a final concentration of 1% glycine, 2% ampholytes (pH 3–10, Pharmacia, Fine Chemicals, Piscataway, N.J.) in 100 milliliter volumes. The solution was added to 4 grams of Ultradex (specially treated Sephadex G-75, LKB, Bromma, Sweden) and spread onto a gel tray. The gel was dried to the appropriate crack point of the Ultradex by gentle blow drying. The tray was then transferred to a cooling plate and electrophoresed for 20–26 hours under a constant current of 7 mA. During electrophoresis the voltage was increased from 100 to 1,000 volts. After the gel reached equilibrium at 1,000 volts, the gel was sectioned into 30 portions, and each portion was transferred into a 1×5 cm column.

The protein in each fraction was eluted into a set of test tubes with 5 milliliters of sterile distilled water. After pH determination, each fraction was dialysed against 1000 milliliter volumes of sterile distilled water to remove ampholytes. IL-2 microassay of each dialysed fraction revealed that IL-2 activity was contained in fractions corresponding to iso-electric values of pH 6.2–7.0. Active fractions were pooled and dialysed against 1000 milliliter volumes of 50 mM ammonium bicarbonate. The ammonium bicarbonate was thereafter removed by lyopholization. Thereafter, the IL-2 was freeze dried and then stored at −70° C.

Sample Preparation for Gel Electrophoresis

Lyophilized IL-2 was resuspended in 10 mM Tris-HCl (pH 8.0), 1 mM ethylenediaminetetradcetic acid (hereafter "EDTA"), 1% by volume 2-mercaptoethanol, 1% by weight sodium dodecyl sulfate (hereafter "SDS"), 0.005% by weight bromophenol blue (as the tracking dye) and 10% by volume glycerol. The mixture was immediately applied to SDS polyacrylamide gels and electrophoresed.

Analytical SDS Polyacrylamide Gel Electrophoresis (hereafter "PAGE")

Gels used were gradients of between 7.5 and 15.0% acrylamide. One millimeter thick gels (180 cm long) with a 10% acrylamide 9 millimeter separation gel and a 5% acrylamide 2 millimeter stacking gel were used to fractionate IL-2. The shock acrylamide solution was 30% by weight and 0.08% by weight N,N' bis-methylene acrylamide. The final concentration of the separation gel was 0.375 M Tris-HCl (pH 8.8), 0.05% TEMED and 0.013% ammonium persulfate. The final concentration of the stacking gel was 0.175 M Tris-HCl (pH 6.8), 0.1% TEMED and 0.5% ammonium persulfate. The electrode buffer was 25 mM Tris-HCl (pH 8.0), 0.1 M glycine and 0.03% SDS.

The molecular weight of IL-2 was determined relative to the following molecular weight standards: bovine serum albumin (mol wt 68,000), ovalbumin (mol wt 43,000), and soybean trypsin inhibitor (mol wt 22,000). After performing a sample application, the gels were run at a constant current of 12.5 mAmp/gel until the dye front ran to the bottom. Following PAGE, the gel was fixed and stained for 20–25 minutes with gentle rocking at room temperature at 0.25% by volume Comassie blue R, 50% by volume methanol, 7.5% by volume acetic acid. The gel was then destained for 1–2 hrs. with rocking at room temperature under multiple changes of 20% by volume ethanol and 7.5% by volume acetic acid. When sufficiently destained to allow visualization of the protein bands, protein present in the stained bands was cut out, electrophoretically eluted and concentrated in final volume 0.5 ml.

SDS-PAGE analysis of IEF fractionated IL-2 revealed some nine to sixteen separate stainable protein bands with molecular weights of between 11,000 to 26,000 daltons. The majority of IL-2 biological activity was electrophoretically eluted from a protein band having a molecular weight of approximately 14,000 daltons. Recovery of biological activity after SDS-PAGE staining and destaining of the slab gel and subsequent electrophoresic elution was about 20–40% of the starting material before electrophoresis.

As will be apparent to those skilled in the art to which the invention is addressed, the present invention may be carried out by using human cell lines, culture media, culture media additives and mitogen stimulants other than those specifically disclosed above, without departing from the spirit or essential characteristics of the invention. The particular processes described above are therefore to be considered in all respects as illustrative and not restrictive, i.e. the scope of the present invention is set forth in the appended claims rather than being limited to the examples of the IL-2 producing processes as set forth in the foregoing description.

What is claimed is:

1. A process for the production of IL-2 from a malignant human T-cell line that is capable of producing IL-2, comprising culturing malignant human T-cells that are capable of producing IL-2 in a culture medium containing a T-cell mitogen and recovering the IL-2 from the culture medium.

2. The process of claim 1, wherein said malignant human T-cells are T leukemic cells or T lymphoma cells.

3. The process of claim 2, wherein said T leukemic cells are Jurkat-FHCRC leukemic human T-cells.

4. The process of claim 2 or 3, wherein the initial T leukemic or T lymphoma cell concentration is in the range of about $1\times 10^5$ to $1\times 10^7$ cells per milliliter.

5. The process of claim 1, 2 or 3, wherein the T-cell mitogen in the culture medium is a compound selected from the group consisting of phytohemagglutinin, concanavalin A or pokeweed mitogen.

6. The process of claim 5, wherein the concentration of phytohemagglutinin mitogen is between 0.5 and 2.0% by volume.

7. The process of claim 5, wherein the concentration of concanavalin A mitogen is between 10 and 100 micrograms per milliliter.

8. The process of claim 5, wherein the culture medium further includes a phorbol ester.

9. The process of claim 8, wherein the phorbol ester is phorbol myristate acetate.

10. The process of claim 9, wherein the phorbol myristate acetate is in a concentration of 10 to 100 nanograms per milliliter.

11. The process of claim 5, wherein the culture medium further includes a medium selected from the group consisting of Roswell Park Memorial Institute medium, Click's medium, and Dulbecco Modified Eagle Medium.

12. The process of claim 5, comprising recovering the IL-2 from the culture medium after approximately 12 to 48 hours of culturing.

13. The process of claim 1, 2 or 3, wherein the culture medium further contains a compound selected from the group consisting of Roswell Park Memorial Institute medium, Click's medium and Dulbecco Modified Eagle Medium.

14. The process of claim 13, wherein the culture medium further contains one or more compounds selected from the group consisting of penicillin, streptomycin, fresh glutamine, Hepes buffer, $NaHCO_3$, fetal calf serum and human serum.

* * * * *

UNITED STATES PATENT AND TRADEMARK OFFICE
CERTIFICATE OF CORRECTION

PATENT NO. : 4,401,756

DATED : August 30, 1983

INVENTOR(S) : Steven Gillis

It is certified that error appears in the above—identified patent and that said Letters Patent is hereby corrected as shown below:

| | | |
|---|---|---|
| Column 1, | line 20 | "Marows" should be — Marrows —. |
| Column 3, | line 27 | "herafter" should be — hereafter —; |
| | line 46 | "supernant" should be — supernate —. |
| Column 4, | line 13 | "Con-A" should be — Con-A‡ —; |
| | line 13 | "PHA" should be — PHA§ —; |
| | line 13 | "PKM" should be — PKM¶ —; |
| | line 30 | "10 µg/ml" should be — ‡10 µg/ml —; |
| | line 31 | "1.0% by volume" should be — §1.0% by volume —; |
| | line 32 | "1/100 dilution" should be — ¶ 1/100 dilution —; |
| | line 60 | Insert — 103 — above "151" (Table II); |

UNITED STATES PATENT AND TRADEMARK OFFICE
CERTIFICATE OF CORRECTION

PATENT NO. : 4,401,756

DATED : August 30, 1983

INVENTOR(S) : Steven Gillis

It is certified that error appears in the above—identified patent and that said Letters Patent is hereby corrected as shown below:

Column 7, line 34    Insert — ‡ — after "medium";

line 35    "-" (first occurrence) should be — § —:

line 41    Insert — ‡ — before "mean";

line 43    "-," should be — § —.

Signed and Sealed this

Seventeenth Day of April 1984

[SEAL]

Attest:

GERALD J. MOSSINGHOFF

Attesting Officer     Commissioner of Patents and Trademarks